United States Patent [19]
Rheinheimer et al.

[11] Patent Number: 4,983,210
[45] Date of Patent: Jan. 8, 1991

[54] ISOXAZOLINES, THEIR PREPARATION AND THEIR USE

[75] Inventors: Joachim Rheinheimer, Ludwigshafen; Karl Eicken, Wachenheim; Hans Theobald, Limburgerhof; Thomas Kuekenhoehner, Frankenthal; Karl-Otto Westphalen, Speyer; Bruno Wuerzer, Otterstadt; Juergen Frank, Schwetzingen; Norbert Meyer, Ladenburg, all of Fed. Rep. of Germany

[73] Assignee: BASF Aktiengesellschaft, Ludwigshafen, Fed. Rep. of Germany

[21] Appl. No.: 326,986

[22] Filed: Mar. 22, 1989

[30] Foreign Application Priority Data

Mar. 23, 1988 [DE] Fed. Rep. of Germany ....... 3809765

[51] Int. Cl.$^5$ ................. C07D 261/04; C07D 403/04; C07D 403/12; A01N 43/80
[52] U.S. Cl. ........................................... 71/94; 71/88; 546/209; 546/275; 548/240
[58] Field of Search ...................... 71/88, 94; 546/275, 546/209; 548/240

[56] References Cited

U.S. PATENT DOCUMENTS 3,631,169  12/1971  Minami et al. .................. 544/137

FOREIGN PATENT DOCUMENTS 0187345  7/1986  European Pat. Off. .
2724677 12/1978  Fed. Rep. of Germany .

OTHER PUBLICATIONS

Cozzi et al., Gazzetta Chimicia Italiana, vol. 116, pp. 717-719 (1986).
Houk et al., J. Am. Chem. Soc., vol. 106, pp. 3880-3882 (1984).
Annunziata et al., Tetrahedron, vol. 42, No. 7, pp. 2129-2134 (1986).

Primary Examiner—Mukund J. Shah
Assistant Examiner—E. Bernhardt
Attorney, Agent, or Firm—Keil and Weinkauf

[57] ABSTRACT

Isoxazolines of the general formula I

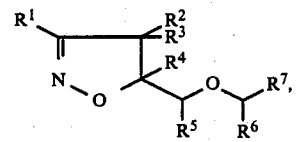

where the substituents have the following meanings:

$R^1$ is $C_1-C_{12}$-alkyl, $C_3-C_7$-cycloalkyl, substituted or unsubstituted phenyl, or a saturated or unsaturated 5- or 6-membered heterocycle;

$R^2$, $R^3$, $R^4$, $R^5$ and $R^6$ are hydrogen, $C_1-C_4$-alkyl or benzyl and $R^7$ is substituted or unsubstituted $C_2-C_6$-alkenyl, $C_5-C_7$-cycloalkenyl, phenyl, naphthyl or thienyl, processes for their manufacture, and their use.

3 Claims, No Drawings

ISOXAZOLINES, THEIR PREPARATION AND THEIR USE

The present invention relates to isoxazolines of the general formula I

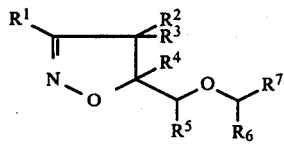

where $R^1$ is $C_1$–$C_{12}$-alkyl, $C_3$–$C_7$-cycloalkyl, phenyl which can carry one to five halogen atoms and/or one to three of the groups $C_1$–$C_4$-alkyl, $C_1$–$C_4$-alkoxy and/or $C_1$–$C_4$-haloalkyl, or a saturated or unsaturated 5-membered or 6membered heterocyclic structure containing a nitrogen, oxygen or sulfur atom as a ring member, $R^2$, $R^3$, $R^4$, $R^5$ and $R^6$ are each hydrogen, $C_1$–$C_4$-alkyl or benzyl and $R^7$ is $C_2$–$C_6$-alkenyl or $C_5$–$C_7$-cycloalkenyl, where these groups may carry one to three phenyl radicals and/or halogen atoms, or is phenyl which may carry one to three of the substituents $C_1$–$C_4$-alkyl, $C_1$–$C_4$-alkoxy, $C_1$–$C_4$-haloalkyl, phenyl or phenoxy, cyano and/or halogen, or is naphthyl or thienyl, where these aromatic rings may carry one to three $C_1$–$C_4$-alkyl groups and/or halogen atoms.

The present invention furthermore relates to processes for the preparation of the compounds I, herbicides which contain these compounds and methods for controlling undesirable plant growth with the compounds I.

DE-A 27 24 677 describes herbicidal 2-(benzyloxymethyl)-tetrahydrofurans. However, because of the poor selectivity with respect to weeds and the relatively high application rates, their action is unsatisfactory.

It is an object of the present invention to provide compounds having improved herbicidal properties.

We have found that this object is achieved by the isoxazolines I defined at the outset. We have furthermore found processes for the preparation of the compounds and methods for controlling undesirable plant growth with these novel compounds.

The compounds I are obtained, for example, by etherifying an appropriately substituted 5-hydroxymethylisoxazoline derivative II with a compound III in a conventional manner in an inert organic solvent in the presence of a base to give an isoxazoline I.

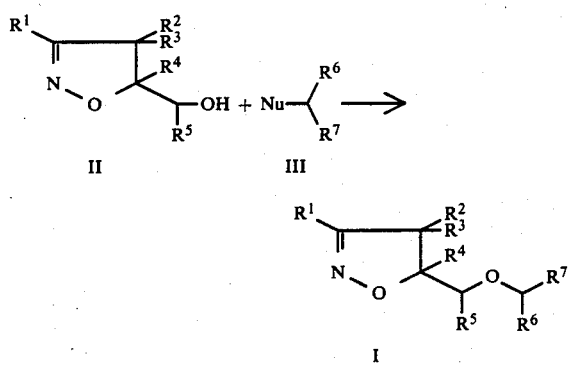

In formula III, Nu is a nucleophilic leaving group, such as chlorine, bromine, iodine, arylsulfonyl or alkylsulfonyl, e.g. toluenesulfonyl, or another equivalent leaving group. Compounds of the formula III having a reactive substituent Nu are known from the literature or are readily obtainable on the basis of the general technical knowledge.

This reaction is generally carried out at from 0° to 120° C., preferably from 10° to 80° C., in an aprotic solvent, preferably in an ether, such as diethyl ether, methyl tert-butyl ether, tetrahydrofuran or dioxane, or dimethyl sulfoxide, dimethylformamide or a mixture of these.

Examples of suitable bases are alkali metal or alkaline earth metal hydrides, such as NaH or $CaH_2$, alkali metal hydroxides, such as NaOH or KOH, alkali metal carbonates, such as $Na_2CO_3$ or $K_2CO_3$, alkali metal amides, such as sodium amide or lithium diisopropylamide, and tertiary amines, such as triethylamine, diisopropylethylamine, N,N-dimethyl-p-aminopyridine, N-methylpyrrolidine, N,N,N',N'-tetramethylethylenediamine, 1,5-diazabicyclo[4.3.0]non-5-ene and 1,8-diazabicyclo[5.4.0]undec-7-ene. The reaction is preferably carried out in the presence of one of the abovementioned inorganic bases.

The reaction can be accelerated by adding a phase-transfer catalyst, such as a crown ether or a quaternary ammonium salt, if heat-sensitive radicals of the educts necessitate mild reaction conditions.

The 5-hydroxymethylisoxazoline derivatives II required for the reaction are obtained in a conventional manner (C. Grundmann, Synthesis 1970, 347 and J. M. J. Trochet, S. Jaccard-Thorndahl, L. Faivre and R. Massard, Helv. Chim. Acta 56 (1973), 1303) from the corresponding oximes IV by reaction with an alkyl alcohol of the formula V,

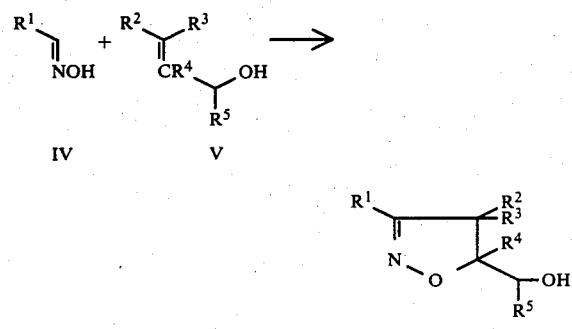

With regard to the use of the novel isoxazolines I in accordance with regulations, preferred substituents are the following radicals: $R^1$ is alkyl, such as methyl, isopropyl, n-butyl, isobutyl, tert-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2dimethylbutyl, 2,3-dimethylbutyl, 3,3-dimethylbutyl, 1-ethylbutyl, 2-ethylbutyl, 1,1,2-trimethylpropyl, 1,2,2trimethylpropyl, 1-ethyl-1-methylpropyl and 1-ethyl-2methylpropyl, in particular methyl, ethyl, propyl, 1-methylethyl, butyl, 1-methylpropyl, 2-methylropyl and 1,1-dimethylethyl; cycloalkyl, such as cyclopropyl, cyclobutyl, cyclopentyl, cyclohexyl and cycloheptyl, in particular cyclopropyl, cyclopentyl and cyclohexyl; phenyl which may be substituted by one to five, in particular one to three, halogen atoms, such as fluorine, chlorine, bromine and/or iodine, in particular fluorine, chlorine or bromine, and/or by one to three of the abovementioned $C_1$-$C_4$-alkyl groups, in particular methyl and ethyl, alkoxy groups, such as methoxy, ethoxy, propoxy, 1-methylethoxy, butoxy, 1-methylpropoxy, 2-methylpropoxy or 1,1-dimethylethoxy, in particular methoxy or ethoxy, and/or haloalkyl groups, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl,2-chloro-2,2-difluoroethyl,2,2-dichloro-2-fluoroethyl, 2,2,2-trichloroethyl or pentafluoroeethyl, in particular difluoromethyl or trifluoromethyl; a saturated or unsatured 5-membered or 6-membered heterocyclic structure, such as tetrahydrofuranyl, tetrahydrothiophenyl, pyrrolidinyl, tetrahydropyranyl, tetrahydrothiopyranyl, piperidyl, furanyl, thienyl, pyrrolyl or pyridyl, in particular tetrahydropyranyl, furyl, thienyl, pyridyl or tetrahydrofuranyl; $R^2$ is benzyl or $C_1$-$C_4$-alkyl as stated under $R^1$, in particular hydrogen, methyl or ethyl; $R^3$ is in general and in particular one of the radicals stated under $R^2$; $R^4$ is in general one of the radicals stated under $R^2$, in particular hydrogen, methyl, ethyl, propyl, 1-methylethyl or benzyl; $R^5$ and $R^6$ are each in general and in particular one of the radicals stated under $R^2$; and $R^7$ is alkenyl, such as ethenyl, 1-propenyl, 2-propenyl, 1-methylethenyl, 1-butenyl, 2-butenyl, 3butenyl, 1-methyl-1-propenyl, 1-methyl-2-propenyl, 2- methyl-1-propenyl, 2-methyl-2-propenyl, 1-pentenyl, 2-pentenyl, 3-pentenyl, 4-pentenyl, 1-methyl-1-butenyl, 2-methyl-1-butenyl,3-methyl-1-butenyl,1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl,1-dimethyl-1-propenyl,1,-dimethyl-2-propenyl 1-dimethyl-1-propenyl,1,2-dimethyl-2-propenyl, 1-ethyl-1-propenyl, 1-ethyl-2-propenyl, 1hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2pentenyl, 1-methyl-3-pentenyl, 2-methyl-3-pentenyl, 3-methyl-3-pentenyl, 4-methyl-3-pentenyl, 1-methyl-4-pentyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2- dimethyl-3-butenyl,2,3-dimethyl-1-butenyl,2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,2,2-trimethyl-2-propenyl, 1-ethyl-1-methyl-2-propenyl, 1-ethyl2-methyl-1-propenyl or 1-ethyl-2-methyl-2-propenyl, in particular ethenyl, 1-methylethyenyl, 2-methyl-1-propenyl or 2-methyl-1-butenyl; $C_5$-$C_7$-cycloalkenyl, such as cyclopentenyl, cyclohexenyl or cycloheptenyl, in particular cyclopentenyl or cyclohexenyl; or phenyl, naphthyl or thienyl, and when $R^7$ is alkenyl or cycloalkenyl it can be substituted by, in particular, phenyl and/or one to three of the halogen atoms stated under $R^1$, when $R^7$ is phenyl it can be substituted by one to three of the abovementioned halogen atoms, $C_1$-$C_4$-haloalkyl groups and/or a phenyl radical, a phenoxy radical and/or cyano groups, and when $R^7$ is naphthyl or thienyl it can be substituted by one to three of the abovementioned $C_1$-$C_4$-alkyl groups and/or halogen atoms.

Particularly preferred compounds I are those in which $R^1$ is straight-chain or branched $C_1$-$C_5$-alkyl, $C_3$-$C_6$-cycloalkyl, tetrahydropyranyl, pyridyl, furyl, phenyl, chlorophenyl, methoxyphenyl or methylphenyl, $R^2$ and $R^3$ are each hydrogen, methyl or ethyl, $R^4$ is hydrogen, straight-chain or branched $C_1$-$C_4$-alkyl or benzyl, $R^5$ and $R^6$ are each hydrogen or methyl and $R^7$ is phenyl, mono-, di- or trichlorophenyl, mono-, di- or trifluorophenyl, mono-, di-or trimethylphenyl, fluorochlorophenyl, 2-fluoro-6methylphenyl, 2,4-difluoro-6-methylphenyl, 2-chloro-6methylphenyl, bromophenyl, mono- or diethylphenyl, phenoxyphenyl, methoxyphenyl, cyanophenyl, trifluoromethylphenyl, naphthyl, thienyl, mono- or dichlorothienyl, methylthienyl, 1-methylethenyl, 1- and 2-methylpropenyl, chloroethenyl or chloropropenyl.

The isoxazolines I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredients.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 10 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 17 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.2% by weight of the active ingredient.

IV. 20 parts by weight of compound no. 29 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 50 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 72 is intimately mixed with 97 parts by weight of particulate kaolin. A dust is obtained containing 3% by weight of the active ingredient.

VII. 30 parts by weight of compound no. 121 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 125 is intimately mixed with 2 parts of the calcium salts of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |

| Botanical name | Common name |
| --- | --- |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the isoxazolines of the formula I may be mixed and applied together with numerous representatives of other herbicidal or growth-regulating active ingredients groups. Examples of suitable components are diazines, 4H-3,1-benzoxazine derivative, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acid derivatives, phenyloxy- or heteroaryloxy-phenylpropionic acids and salts, esters and amides thereof, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were employed, after appropriate modifications to the starting materials, to obtain further compounds of the formula I; the compounds obtained are listed in the tables below with physical data. Those compounds for which no data are given may be produced analogously from the appropriate materials. In view of their close structural similarity with the compounds produced and investigated, they are expected to have a similar action.

EXAMPLE 1

Manufacturing example for a starting material of the formula II: 5-hydroxymethyl-5-methyl-3-phenyl-4,5-dihydro-1,2-oxazole At 10° C., 380 g of a 10% strength sodium hypochloride solution in which 0.3 g of sodium hydroxide is additionally dissolved is added dropwise to 50.0 g of benzaldoxime and 37.2 g of 2-methyl-2-propenol in 80 ml of diethyl ether. The mixture is stirred overnight at room temperature, the organic phase is separated off and extracted 5 times, each time with 100 ml of diethyl ether, and the extracts are dried over sodium sulfate and evaporated down. There remains 72.3 g of crude product, which is distilled at 140° C./0.01 mbar. Melting point: 49°–50° C. Further 4,5-dihydro-1,2-oxazoles may be prepared analogously.

EXAMPLE 2

General manufacturing example for isoxazolines of the formula I:

0.12 mol of sodium hydride is added to 50 ml of a 1:1 mixture of tetrahydrofuran and dimethylformamide. At room temperature, a solution of 0.10 ml of a 5-hydroxymethyl-4,5-dihydro-1,2-oxazole in 80 ml of a 1:1 mixture of tetrahydrofuran and dimethylformamide is then dripped in and the mixture is stirred for 1 hour at 60° C. Subsequently, a solution of 0.1 mol of the particular benzyl or allyl halide in 20 ml of the same solvent mixture is dripped in at room temperature. In many cases, the mixture has to be stirred for a further 2 hours at 60° C. to complete the conversion. The mixture is then stirred into 1 liter of ice water, extracted, dried and evaporated down. The crude product may be purified further by chromatography over silica gel or distillation under reduced pressure.

TABLE

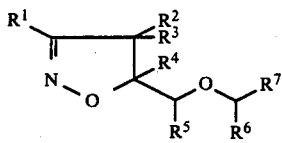

| No. | R¹ | R² | R³ | R⁴ | R⁵ | R⁶ | R⁷ | Phys. data |
|---|---|---|---|---|---|---|---|---|
| 1 | methyl | H | H | $CH_3$ | H | H | phenyl | |
| 2 | methyl | H | H | $CH_3$ | H | H | 2-methylphenyl | |
| 3 | methyl | H | H | $CH_3$ | H | H | 2-fluorophenyl | |
| 4 | ethyl | H | H | $CH_3$ | H | H | phenyl | |
| 5 | ethyl | H | H | $CH_3$ | H | H | 2-methylphenyl | ¹H: 1.13(t), 1.38(s), 2.20–2.40 (m), 2.35(s) |
| 6 | ethyl | H | H | $CH_3$ | H | H | 2-chlorophenyl | |
| 7 | ethyl | H | H | $CH_3$ | H | H | 2-chloro-6-fluorophenyl | $n_D^{24} = 1.5102$ |
| 8 | ethyl | H | H | $CH_3$ | H | H | 2-fluorophenyl | |
| 9 | isopropyl | H | H | $CH_3$ | H | H | phenyl | |
| 10 | isopropyl | H | H | $CH_3$ | H | H | 2-chlorophenyl | |
| 11 | isopropyl | H | H | $CH_3$ | H | H | 2-fluorophenyl | ¹H: 1.10(d), 1.37(s), 2.60(d), 3.00(d), 4.55(s) |
| 12 | isopropyl | H | H | $CH_3$ | H | H | 2-chloro-6-fluorophenyl | $n_D^{23} = 1.5058$ |
| 13 | isopropyl | H | H | $CH_3$ | H | H | 3-phenoxyphenyl | $n_D^{23} = 1.5425$ |
| 14 | isopropyl | H | H | $CH_3$ | H | H | 2-cyanophenyl | $n_D^{23} = 1.5214$ |
| 15 | isopropyl | H | H | $CH_3$ | H | H | 2-methoxyphenyl | $n_D^{24} = 1.5106$ |
| 16 | isopropyl | H | H | $CH_3$ | H | H | 2-trifluoromethylphenyl | $n_D^{23} = 1.4731$ |
| 17 | isopropyl | H | H | $CH_3$ | H | H | 2,4-difluorophenyl | $n_D^{24} = 1.4854$ |
| 18 | isopropyl | H | H | $CH_3$ | H | H | 1-naphthyl | $n_D^{23} = 1.5594$ |
| 19 | isopropyl | H | H | $CH_3$ | H | H | 2,4,6-trimethylphenyl | $n_D^{23} = 1.5035$ |
| 20 | isopropyl | H | H | $CH_3$ | H | H | 2-thienyl | $n_D^{22} = 1.5145$ |
| 21 | isopropyl | H | H | $CH_3$ | H | H | 3-chloro-2-thienyl | |
| 22 | isopropyl | H | H | $CH_3$ | H | H | 2-chloro-4-thienyl | |
| 23 | isopropyl | H | H | $CH_3$ | H | H | 1-methylethenyl | $n_D^{24} = 1.4554$ |
| 24 | isopropyl | H | H | $CH_3$ | H | H | 2-methylpropen-1-yl | $n_D^{23} = 1.4604$ |
| 25 | isopropyl | H | H | $CH_3$ | H | H | 2-chloropropen-1-yl | |
| 26 | 1-methylpropyl | H | H | $CH_3$ | H | H | phenyl | |
| 27 | 1-methylpropyl | H | H | $CH_3$ | H | H | 2-chlorophenyl | |
| 28 | 1-methylpropyl | H | H | $CH_3$ | H | H | 2-fluorophenyl | |
| 29 | 1-methylpropyl | H | H | $CH_3$ | H | H | 2-methylphenyl | ¹H: 0.80–1.00(m), 1.43(s), 3.40–3.55(m), 4.57(cm). |
| 30 | 1-methylpropyl | H | H | $CH_3$ | H | H | 2-chloro-6-fluorophenyl | $n_D^{24} = 1.5030$ |
| 31 | 1-methylpropyl | H | H | $CH_3$ | H | H | 2,4-difluorophenyl | |
| 32 | 2-methylpropyl | H | H | $CH_3$ | H | H | phenyl | |
| 33 | 2-methylpropyl | H | H | $CH_3$ | H | H | 2-methylphenyl | $n_D^{24} = 1.5023$ |
| 34 | 2-methylpropyl | H | H | $CH_3$ | H | H | 2-chlorophenyl | |
| 35 | 2-methylpropyl | H | H | $CH_3$ | H | H | 2-fluorophenyl | |
| 36 | 2-methylpropyl | H | H | $CH_3$ | H | H | 2-chloro-6-fluorophenyl | $n_D^{24} = 1.5031$ |
| 37 | cyclopropyl | H | H | $CH_3$ | H | H | phenyl | |
| 38 | cyclopropyl | H | H | $CH_3$ | H | H | 2-methylphenyl | $n_D^{23} = 1.9256$ |
| 39 | cyclopropyl | H | H | $CH_3$ | H | H | 2-chlorophenyl | |
| 40 | cyclopropyl | H | H | $CH_3$ | H | H | 2-fluorophenyl | |
| 41 | cyclopropyl | H | H | $CH_3$ | H | H | 2,4-difluorophenyl | |
| 42 | cyclopropyl | H | H | $CH_3$ | H | H | 2-chloro-6-fluorophenyl | $n_D^{23} = 1.5231$ |
| 43 | cyclopentyl | H | H | $CH_3$ | H | H | phenyl | |
| 44 | cyclopentyl | H | H | $CH_3$ | H | H | 2-methylphenyl | $n_D^{24} = 1.5232$ |
| 45 | cyclopentyl | H | H | $CH_3$ | H | H | 2-chlorophenyl | |
| 46 | cyclopentyl | H | H | $CH_3$ | H | H | 2-fluorophenyl | |
| 47 | cyclopentyl | H | H | $CH_3$ | H | H | 2-chloro-6-fluorophenyl | $n_D^{24} = 1.5210$ |
| 48 | cyclopentyl | H | H | $CH_3$ | H | H | 2,4-difluorophenyl | |
| 49 | phenyl | H | H | $CH_3$ | H | H | phenyl | |
| 50 | phenyl | H | H | $CH_3$ | H | H | 2-methylphenyl | $n_D^{24} = 1.5710$ |
| 51 | phenyl | H | H | $CH_3$ | H | H | 2-chlorophenyl | |
| 52 | phenyl | H | H | $CH_3$ | H | H | 2-chloro-6-fluorophenyl | ¹H: 1.47(s), 2.95(d), 3.45(d) 4.75 (s) |
| 53 | phenyl | H | H | $CH_3$ | H | H | 2-fluorophenyl | |
| 54 | 4-tetrahydropyranyl | H | H | $CH_3$ | H | H | phenyl | |
| 55 | 4-tetrahydropyranyl | H | H | $CH_3$ | H | H | 2-methylphenyl | $n_D^{23} = 1.5246$ |
| 56 | 4-tetrahydropyranyl | H | H | $CH_3$ | H | H | 2-chlorophenyl | |
| 57 | 4-tetrahydropyranyl | H | H | $CH_3$ | H | H | 2-fluorophenyl | |
| 58 | 4-tetrahydropyranyl | H | H | $CH_3$ | H | H | 2-chloro-6-fluorophenyl | $n_D^{23} = 1.5236$ |
| 59 | 3-tetrahydropyranyl | H | H | $CH_3$ | H | H | 2-methylphenyl | $n_D^{23} = 1.5234$ |
| 60 | methyl | H | H | H | $CH_3$ | H | 2-chloro-6-fluorophenyl | bp.$_{0.4}$ = 158–160 |
| 61 | methyl | H | H | H | $CH_3$ | H | 2,6-dichlorophenyl | bp.$_{0.2}$ = 158–160 |
| 62 | methyl | H | H | H | $CH_3$ | H | 2-chlorophenyl | bp.$_{0.3}$ = 150–152 |
| 63 | ethyl | H | H | H | H | H | 4-chloro-2-fluorophenyl | bp.$_{0.4}$ = 163–165 |
| 64 | ethyl | H | H | H | H | H | 2,3,6-trichlorophenyl | bp.$_{0.3}$ = 208–210 |
| 65 | ethyl | H | H | H | H | H | 2-chlorophenyl | bp.$_{0.3}$ = 158–160 |
| 66 | ethyl | H | H | H | H | H | 2,6-dichlorophenyl | bp.$_{0.2}$ = 183–185 |
| 67 | ethyl | H | H | H | H | H | 2-chloro-6-fluorophenyl | bp.$_{0.2}$ = 157–158 |
| 68 | ethyl | H | H | H | H | H | phenyl | bp.$_{0.4}$ = 148–150 |
| 69 | ethyl | H | H | H | H | H | 2-methylphenyl | bp.$_{0.4}$ = 162–164 |

TABLE-continued

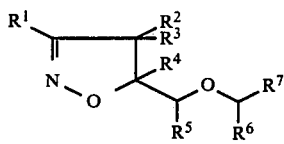

| No. | R¹ | R² | R³ | R⁴ | R⁵ | R⁶ | R⁷ | Phys. data |
|---|---|---|---|---|---|---|---|---|
| 70 | methyl | H | H | H | H | H | phenyl | $bp._{0.1} = 126-128$ |
| 71 | methyl | H | H | H | H | H | 2-methylphenyl | $bp._{0.06} = 146-148$ |
| 72 | methyl | H | H | H | H | H | 2-chloro-6-fluorophenyl | $bp._{0.05} = 166-168$ |
| 73 | methyl | H | H | H | H | H | 2,6-dichlorophenyl | $bp._{2} = 192-194$ |
| 74 | methyl | H | H | H | H | H | 2-chlorophenyl | $bp._{0.05} = 156-158$ |
| 75 | methyl | H | H | H | H | H | 4-chloro-2-fluorophenyl | $bp._{0.3} = 156-158$ |
| 76 | methyl | H | H | H | H | H | 2,3,6-trichlorophenyl | $bp._{0.5} = 208-210$ |
| 77 | methyl | H | H | H | H | H | 2-chloro-4-flourophenyl | $bp._{0.06} = 160-162$ |
| 78 | methyl | H | H | H | H | H | 4-fluorophenyl | $bp._{0.05} = 144-146$ |
| 79 | methyl | H | H | H | H | H | 2,4-dichlorophenyl | $bp._{0.4} = 172-174$ |
| 80 | methyl | H | H | H | H | H | 3,4-dichlorophenyl | $bp._{1.2} = 184-187$ |
| 81 | isopropyl | H | H | CH₃ | H | H | 2,6-difluorophenyl | $n_D^{23} = 1.4848$ |
| 82 | isopropyl | H | H | CH₃ | H | H | 2,6-dimethylphenyl | $n_D^{23} = 1.5075$ |
| 83 | 1-methylpropyl | H | H | CH₃ | H | H | 3-chloro-2-thienyl | $n_D^{24} = 1.5045$ |
| 84 | 1-methylpropyl | H | H | CH₃ | H | H | 2-chloro-4-thienyl | $n_D^{24} = 1.5240$ |
| 85 | 1-methylpropyl | H | H | CH₃ | H | H | 2-trifluoromethylphenyl | $n_D^{24} = 1.4716$ |
| 86 | 3-tetrahydropyranyl | H | H | CH₃ | H | H | 2-chloro-6-fluorophenyl | $n_D^{23} = 1.5212$ |
| 87 | 3-tetrahydropyranyl | H | H | CH₃ | H | H | 2-fluorophenyl | |
| 88 | n-propyl | H | H | CH₃ | H | H | phenyl | |
| 89 | n-propyl | H | H | CH₃ | H | H | 2-methylphenyl | |
| 90 | n-propyl | H | H | CH₃ | H | H | 2-chloro-6-fluorophenyl | |
| 91 | n-propyl | H | H | CH₃ | H | H | 2-fluorophenyl | |
| 92 | n-propyl | H | H | CH₃ | H | H | 2-bromophenyl | |
| 93 | t-butyl | H | H | CH₃ | H | H | 2-chloro-6-fluorophenyl | $n_D^{22} = 1.5010$ |
| 94 | t-butyl | H | H | CH₃ | H | H | 2-methylphenyl | $n_D^{22} = 1.5020$ |
| 95 | t-butyl | H | H | CH₃ | H | H | 2-fluorophenyl | |
| 96 | t-butyl | H | H | CH₃ | H | H | 2-ethylphenyl | |
| 97 | t-butyl | H | CH₃ | CH₃ | H | H | 2-methylphenyl | |
| 98 | phenyl | CH₃ | CH₃ | CH₃ | H | H | 2-methylphenyl | |
| 99 | isopropyl | H | H | ethyl | H | H | 2-methylphenyl | $n_D^{24} = 1.5050$ |
| 100 | isopropyl | H | H | ethyl | H | H | 2-chloro-6-fluorophenyl | $n_D^{24} = 1.5036$ |
| 101 | isopropyl | H | H | ethyl | H | CH₃ | 2-chloro-6-fluorophenyl | |
| 102 | isopropyl | H | H | benzyl | H | H | 2-methylphenyl | |
| 103 | isopropyl | H | H | benzyl | H | H | 2-chloro-6-fluorophenyl | $n_D^{24} = 1.5420$ |
| 104 | isopropyl | H | H | benzyl | H | H | 2-fluorophenyl | |
| 105 | isopropyl | H | H | i-propyl | H | H | 2-methylphenyl | $n_D^{24} = 1.5049$ |
| 106 | isopropyl | H | H | i-propyl | H | H | 2-chloro-6-fluorophenyl | $n_D^{24} = 1.5035$ |
| 107 | 2-furyl | H | H | CH₃ | H | H | 2-chloro-6-fluorophenyl | |
| 108 | 2-furyl | H | H | CH₃ | H | H | 2-methylphenyl | |
| 109 | 2-thienyl | H | H | CH₃ | H | H | 2-methylphenyl | |
| 110 | 3-pyridyl | H | H | CH₃ | H | H | 2-methylphenyl | |
| 111 | 3-pyridyl | H | H | CH₃ | H | H | 2-chloro-6-fluorophenyl | |
| 112 | 2-chlorophenyl | H | H | CH₃ | H | H | 2-methylphenyl | |
| 113 | 2-chlorophenyl | H | H | CH₃ | H | H | 2-chloro-6-fluorophenyl | $n_D^{24} = 1.5705$ |
| 114 | 3-chlorophenyl | H | H | CH₃ | H | H | 2-methylphenyl | |
| 115 | 4-chlorophenyl | H | H | CH₃ | H | H | 2-fluorophenyl | |
| 116 | 2-methoxyphenyl | H | H | CH₃ | H | H | 2-methylphenyl | |
| 117 | 2-methoxyphenyl | H | H | CH₃ | H | H | 2-chloro-6-fluorophenyl | |
| 118 | 2-methoxyphenyl | H | H | CH₃ | H | H | phenyl | |
| 119 | isopropyl | H | H | n-propyl | H | H | 2-methylphenyl | |
| 120 | n-butyl | H | H | CH₃ | H | H | 2-chloro-6-fluorophenyl | |
| 121 | isopropyl | H | H | CH₃ | H | H | 2-methylphenyl | ¹H: 1.10(d), 1.37(s), 2.30(s), 4.60(mc) |
| 122 | isopropyl | H | H | H | H | H | 4-fluorophenyl | ¹H: 1.15(d), 2.60-3.10(m), 4.55(s) |
| 123 | isopropyl | H | H | H | H | H | 2-methylphenyl | ¹H: 1.12(d), 2.32(s), 2.60-3.10(m) 3.45-3.65(m), 4.55(s) 4.60-4.80(m). |
| 124 | methyl | H | H | H | H | H | 2-fluorophenyl | $n_D^{24} = 1.5094$ |
| 125 | isopropyl | H | H | CH₃ | H | CH₃ | phenyl | $n_D^{23} = 1.4850$ |
| 126 | 2-chlorophenyl | H | H | CH₃ | H | H | 2-fluorophenyl | $n_D^{25} = 1.5642$ |
| 127 | 2-methoxyphenyl | H | H | CH₃ | H | H | 2-chlorophenyl | $n_D^{23} = 1.5784$ |
| 128 | isopropyl | H | H | benzyl | H | H | phenyl | $n_D^{24} = 1.5425$ |

*refractive indexes ($n_D$), boiling points (Kp) in C.° or selected ¹H-NMR signals: δ in ppm using tetramethylsilane as internal standard (¹H).

USE EXAMPLES

The action of the isoxazolines of the formula I on plant growth is demonstrated by the following greenhouse experiments:

The vessels employed were plastic flowerpots having a volume of 300 cm³ and filled with a sandy loam containing about 3.0% humus. The seeds of the test plants were sown separately, according to species.

For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients. The application rates were 0.5 and 1.0 kg/ha.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated. The application rate for postemergence treatment was 1.0 kg/ha. No covers were placed on the vessels in this method.

The pots were set up in the greenhouse, species from warmer climates in warmer areas (20° to 35° C.) and species from moderate climates at 10° to 20 ° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were:

| Abbrev. | Botanical name | Common name |
| --- | --- | --- |
| BRNSW | Brassica napus | rapeseed |
| BROIN | Bromus inermis | smooth broome |
| CHEAL | Chenopodium album | lambsquarters (goosefoot) |
| ELEIN | Eleusine indica | |
| ECHCG | Echinochloa crus-galli | barnyardgrass |
| HELAN | Helianthus annus | sunflowers |
| LOLMU | Lolium multiflorum | annual ryegrass |
| POAAN | Poa annua | annual bluegrass |

The compounds of Examples 7 and 12, applied preemergence at a rate of 1.0 kg/ha, combated unwanted plants extremely well, and were well tolerated by rape.

Compound no. 52, applied postemergence at a rate of 1.0 kg/ha, had a herbicidal action on Chenopodium album without damaging crop plants.

Compound no. 42, applied preemergence at a rate of 0.5 kg/ha, had a very good herbicidal action of broad-leaved plants without damaging, for instance, sunflowers.

We claim:

1. An isoxazoline of the formula I

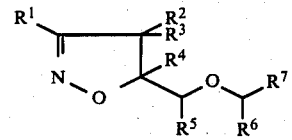

where the substituents have the following meanings:
$R^1$ is phenyl substituted by from one to five halogens and from one to three of the groups $C_1$-$C_4$-alkyl, $C_1$-$C_4$-alkoxy or $C_1$-$C_4$-haloalkyl; or phenyl substituted by from one to five halogens or by from one to three of the groups $C_1$-$C_4$-alkyl, $C_1$-$C_4$-alkoxy or $C_1$-$C_4$-haloalkyl $R^2$, $R^3$, $R^4$, $R^5$ and $R^6$ are hydrogen, $C_1$-$C_4$-alkyl or benzyl and $R^7$ is $C_2$-$C_6$-alkenyl or $C_5$-$C_7$-cycloalkenyl, or $C_2$-$C_6$-alkenyl or $C_5$-$C_7$-cycloalkenyl substituted by one to three phenyl radicals and halogen atoms, or $C_2$-$C_6$-alkenyl or $C_5$-$C_7$-cycloalkenyl substituted by one to three; phenyl radicals or halogen atoms; unsubstituted phenyl or phenyl substituted by from one to three of the following substituents: $C_1$-$C_4$-alkyl, $C_1$-$C_4$-alkoxy, $C_1$-$C_4$-haloalkyl, phenyl, phenoxy, cyano and halogen; or unsubstituted naphthyl or thienyl, or naphthyl or thienyl substituted by from one to three $C_1$-$C_4$-alkyl groups and halogen atoms, or naphthyl or thienyl substituted by from one to three $C_1$-$C_4$-alkyl groups or halogen atoms.

2. A process for combating the growth of unwanted plants, wherein the unwanted plants or their habitat are treated with a herbicidally effective amount of an isoxazoline of the formula I

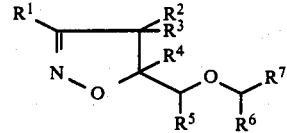

where the substituents have the following meanings:
$R^1$ is $C_1$-$C_{12}$-alkyl, $C_3$-$C_7$-cycloalkyl, unsubstituted phenyl or phenyl substituted by from one to five halogens and from one to three of the groups $C_1$-$C_4$-alkyl, $C_1$-$C_4$-alkoxy or $C_1$-$C_4$-haloalkyl; or phenyl substituted by from one to five halogens or by from one to three of the group $C_1$-$C_4$-alkyl, $C_1$-$C_4$-alkoxy or $C_1$-$C_4$-haloalkyl; or $R^1$ is tetrahydrofuranyl, tetrahydrothiophenyl, pyrrolidinyl, tetrahydropyranyl, tetrahydrothiopyranyl, piperidyl, furanyl, thienyl, pyrrolyl or pyridyl directly attached to the 3-position of the isoxazoline ring;

$R^2$, $R^3$, $R^4$, $R^5$ and $R^6$ are hydrogen, $C_1$-$C_4$-alkyl or benzyl and $R^7$ is $C_2$-$C_6$-alkenyl or $C_5$-$C_7$-cycloalkenyl, or $C_2$-$C_6$-alkenyl or $C_5$-$C_7$-cycloalkenyl substituted by one to three phenyl radicals or halogen atoms; unsubstituted phenyl or phenyl substituted by from one to three of the following substituents: $C_1$-$C_4$-alkyl, $C_1$-$C_4$-alkoxy, $C_1$-$C_4$-haloalkyl, phenyl, phenoxy, cyano and halogen; or unsubstituted naphthyl or thienyl, or naphthyl or thienyl substituted by from one to three $C_1$-$C_4$-alkyl groups and halogen atoms, or naphthyl or thienyl substituted by one to three $c_1$-$C_4$-alkyl groups or halogen atoms.

3. A herbicidal composition containing a herbicidally effective amount of the isoxazoline of the formula I in claim 2, along with an inert carrier or diluent.

* * * * *